United States Patent
Plumptre

(10) Patent No.: US 8,790,315 B2
(45) Date of Patent: *Jul. 29, 2014

(54) DOSE SETTING MECHANISM FOR A DRUG DELIVERY DEVICE

(75) Inventor: David Plumptre, Droitwich Spa (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 243 days.

This patent is subject to a terminal disclaimer.

(21) Appl. No.: 13/375,185

(22) PCT Filed: May 28, 2010

(86) PCT No.: PCT/EP2010/057495
§ 371 (c)(1),
(2), (4) Date: Mar. 12, 2012

(87) PCT Pub. No.: WO2010/139645
PCT Pub. Date: Dec. 9, 2010

(65) Prior Publication Data
US 2012/0165751 A1 Jun. 28, 2012

Related U.S. Application Data

(60) Provisional application No. 61/182,822, filed on Jun. 1, 2009.

(30) Foreign Application Priority Data

Jul. 10, 2009 (EP) ..................................... 09009056

(51) Int. Cl.
A61M 5/00 (2006.01)
A61M 5/315 (2006.01)

(52) U.S. Cl.
CPC ....... *A61M 5/31551* (2013.01); *A61M 5/31541* (2013.01); *A61M 5/31511* (2013.01)
USPC ......................................................... 604/207

(58) Field of Classification Search
CPC .............. A61M 5/315; A61M 5/3155; A61M 5/31551; A61M 5/31528
USPC ......................................... 604/187, 207–211
See application file for complete search history.

(56) References Cited

U.S. PATENT DOCUMENTS 3,302,462 A 2/1967 Pursell
5,514,097 A 5/1996 Knauer
(Continued)

FOREIGN PATENT DOCUMENTS

DE 93 01 334 U1 4/1993
DE 197 30 999 C1 12/1998
(Continued)

OTHER PUBLICATIONS

European Search Report for EP Application No. 09009056, dated Jun. 17, 2010.
(Continued)

*Primary Examiner* — Theodore Stigell
(74) *Attorney, Agent, or Firm* — McDonnell Boehnen Hulbert & Berghoff LLP

(57) ABSTRACT

The invention relates to a dose setting mechanism, which is operable to be coupled to a medication cartridge and which comprises means that prevent the user from setting a dose greater than the remaining medication in the cartridge. The dose setting mechanism comprises a shaft. A helical groove having a first pitch is provided along a first portion of the shaft. The dose setting mechanism further comprises a nut member disposed on the helical groove of said shaft. During dose setting, the shaft is rotated relative to the nut member while the nut member traverses along the groove from a distal end of the shaft towards a proximal end of the shaft. The mechanism further comprises means preventing a user of said dose setting mechanism from setting a dose of said medication that is greater than said remaining medication in said cartridge, said means comprising a second pitch provided along a second portion of said shaft, wherein said first pitch is different from said second pitch, wherein said second pitch is preferably greater than said first pitch.

12 Claims, 6 Drawing Sheets

(56) References Cited

U.S. PATENT DOCUMENTS

| | | | |
|---|---|---|---|
| 5,584,815 | A | 12/1996 | Pawelka et al. |
| 5,591,136 | A | 1/1997 | Gabriel |
| 5,792,117 | A | 8/1998 | Brown |
| 5,820,602 | A | 10/1998 | Kovelman et al. |
| 6,090,080 | A | 7/2000 | Jost et al. |
| 6,936,032 | B1 | 8/2005 | Bush, Jr. et al. |
| 2004/0127858 | A1 | 7/2004 | Bendek et al. |
| 2004/0162528 | A1 | 8/2004 | Horvath et al. |
| 2004/0186437 | A1 | 9/2004 | Frenette et al. |
| 2004/0210199 | A1 | 10/2004 | Atterbury et al. |
| 2004/0236285 | A1 | 11/2004 | Fisher et al. |
| 2005/0137571 | A1 | 6/2005 | Hommann |
| 2006/0153693 | A1 | 7/2006 | Fiechter |
| 2006/0258988 | A1 | 11/2006 | Keitel et al. |
| 2007/0021718 | A1 | 1/2007 | Burren et al. |
| 2008/0027397 | A1 | 1/2008 | DeRuntz et al. |
| 2008/0077095 | A1 | 3/2008 | Kirchhofer |
| 2008/0208123 | A1 | 8/2008 | Hommann |
| 2009/0227959 | A1 | 9/2009 | Hirschel et al. |
| 2010/0324494 | A1* | 12/2010 | Plumptre ............ 604/207 |

FOREIGN PATENT DOCUMENTS

| | | |
|---|---|---|
| DE | 298 18 721 U1 | 3/2000 |
| DE | 10 2005 063 311 | 8/2006 |
| DE | 10 2005 060 928 | 6/2007 |
| DE | 10 2006 038 123 | 2/2008 |
| DE | 10 2007 026 083 | 11/2008 |
| EP | 0 897 728 | 2/1999 |
| EP | 0 937 471 | 8/1999 |
| EP | 0 937 472 | 8/1999 |
| EP | 1 541 185 | 6/2005 |
| EP | 1 776 975 | 4/2007 |
| EP | 1 923 084 | 5/2008 |
| GB | 2 443 390 | 5/2008 |
| WO | 92/18180 | 10/1992 |
| WO | 93/07922 | 4/1993 |
| WO | 96/23973 | 8/1996 |
| WO | 96/39214 | 12/1996 |
| WO | 97/10864 | 3/1997 |
| WO | 99/03520 | 1/1999 |
| WO | 01/19434 | 3/2001 |
| WO | 03/080160 | 10/2003 |
| WO | 2004/020028 | 3/2004 |
| WO | 2004/064902 | 8/2004 |
| WO | 2004/078241 | 9/2004 |
| WO | 2004/078242 | 9/2004 |
| WO | 2004/078293 | 9/2004 |
| WO | 2005/018721 | 3/2005 |
| WO | 2005/021072 | 3/2005 |
| WO | 2005/044346 | 5/2005 |
| WO | 2005/123159 | 12/2005 |
| WO | 2006/024461 | 3/2006 |
| WO | 2006/058883 | 6/2006 |
| WO | WO 2006/058883 * | 6/2006 |
| WO | 2006/079481 | 8/2006 |
| WO | 2006/089767 | 8/2006 |
| WO | 2006/114395 | 11/2006 |
| WO | 2006/125328 | 11/2006 |
| WO | 2007/017052 | 2/2007 |
| WO | 2007/067889 | 6/2007 |
| WO | 2008/031235 | 3/2008 |
| WO | 2008/074897 | 6/2008 |
| WO | 2008/116766 | 10/2008 |
| WO | 2008/128373 | 10/2008 |

OTHER PUBLICATIONS

International Search Report for International App. No. PCT/EP2010/057495, completed Jun. 30, 2010.
International Preliminary Report on Patentability for International App. No. PCT/EP2010/057495, completed Jul. 20, 2011.

\* cited by examiner

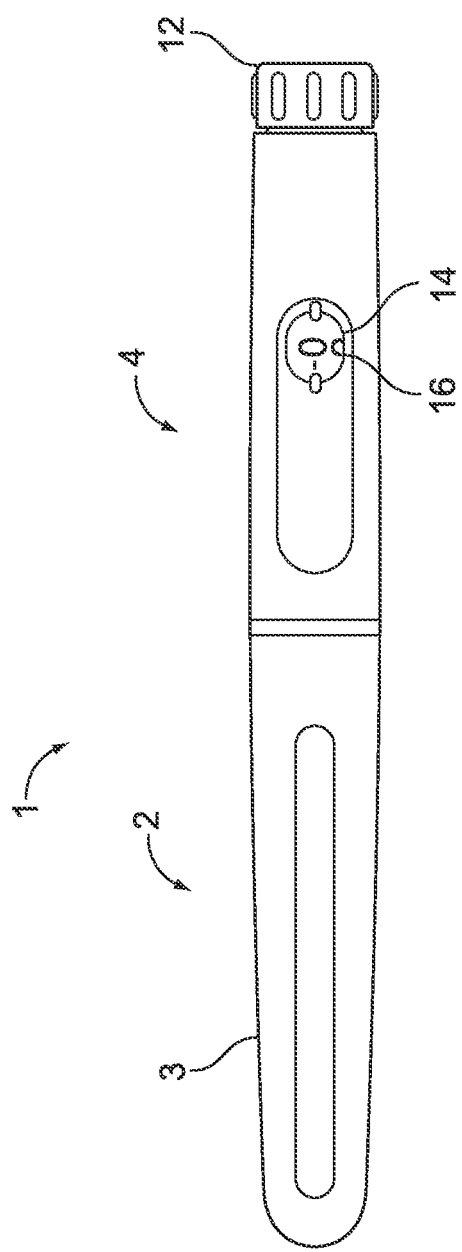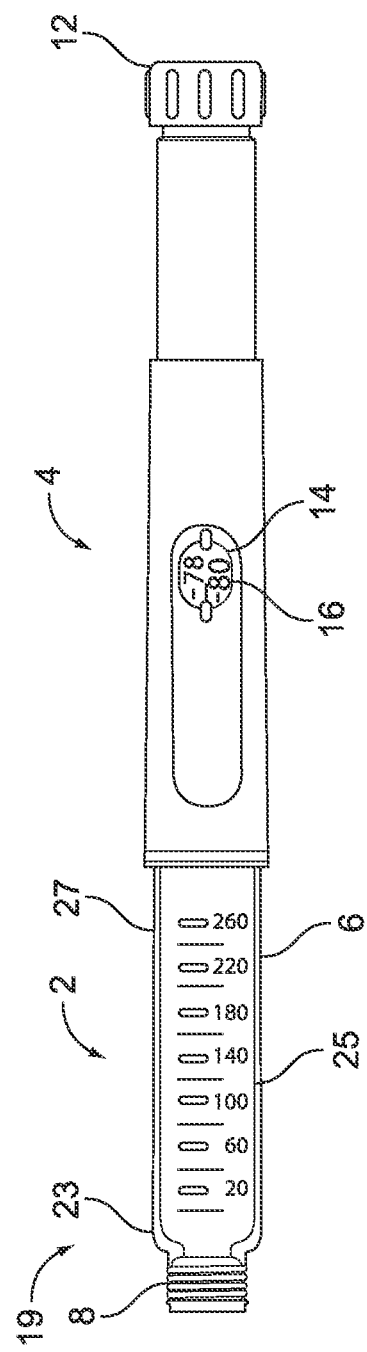

DOSE SETTING MECHANISM FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2010/057495 filed _May 28, 2010, which claims priority to U.S. Provisional Patent Application No. 61/182, 822 filed on Jun. 1, 2009 and to European Patent Application No. 09009056.4 filed Jul. 10, 2009. The entire disclosure contents of these applications are herewith incorporated by reference into the present application.

FIELD OF INVENTION

The present patent application is generally directed to drug delivery devices. More particularly, the present patent application is generally directed to drug delivery devices, such as pen type drug delivery devices. Such devices provide for self administration of medicinal product from a multi-dose cartridge and permit a user to set the delivery dose. The present application may find application in both resettable (i.e., reusable) and non-resettable (i.e., non-reusable) type drug delivery devices. However, aspects of the invention may be equally applicable in other scenarios as well.

BACKGROUND

Pen type drug delivery devices have application where regular injection by persons without formal medical training occurs. This is increasingly common among patients having diabetes where self-treatment enables such patients to conduct effective management of their disease.

In certain types of medication delivery devices, such as pen type devices, cartridges of medication are used. These cartridges are housed in a cartridge holder or cartridge housing. Such cartridges include a bung or stopper at one end. At the other end of the cartridge, the cartridge comprises a pierceable seal. To dispense a dose of medication from such a cartridge, the medication delivery device has a dose setting mechanism that uses a spindle to move in a distal direction towards the cartridge and to press a distal end of the spindle against the bung. This expels a certain set dose of medication from the cartridge. As medication runs low, a user may attempt to set a dose that exceeds the amount of medication left in the cartridge. In order to insure dose accuracy, it is important that a drug delivery device is designed to not allow a user to dial a dose that is greater than the amount of medication remaining in the cartridge. As some users may apply a large turning force (i.e., a large torque load) when attempting to dial a dose that exceeds the amount of medication left in the cartridge, it is important that the drug delivery device be able to withstand a large force.

There is, therefore, a general need to take these perceived dose accuracy issues into consideration when designing either resettable or non-resettable drug delivery devices, such as pen type drug delivery devices.

It is therefore an object of the present invention to provide a dose setting mechanism for a drug delivery device which is improved with regard to above explained needs.

SUMMARY

According to an exemplary arrangement, a dose setting mechanism for a drug delivery device is provided. The dose setting mechanism for a drug delivery device with a cartridge is operable to select a dose of medication which shall be administered out of the cartridge of medication. The dose setting mechanism further comprises means that prevent a user of the dose setting mechanism from setting a dose of medication that is greater than the medication remaining in the cartridge. The dose setting mechanism comprises a shaft and a nut member disposed on a helical groove of the shaft, wherein the helical groove comprises a first pitch which is provided along a first portion of the rotatable shaft. The means preventing a user from setting a dose that is greater than said remaining medication in the cartridge comprise a second pitch which is provided along a second portion of the shaft. The first pitch is different from the second pitch, wherein the second pitch is preferably greater.

During dose setting, the shaft is rotated relative to the nut member while the nut member traverses along the groove from a distal end of the shaft towards a proximal end of the shaft. The nut member traverses along the groove until the user attempts to select a dose greater than the medication remaining in the cartridge and the nut member prevents the shaft and the nut from rotating relative to each other and increasing the dose.

In a preferred embodiment, the nut member and the shaft each comprise at least one substantially radial stop face, wherein the at least one substantially radial stop face of the nut member engages the at least one substantially radial stop face of the shaft preventing the shaft and the nut member from rotating relative to each other in a position preventing a user from setting a dose of the medication greater than the remaining medication in the cartridge. The increased second pitch located preferably at the end of the thread of the shaft just before the radial stop faces engage allows the increase of the effective length of the stop faces in axial direction and therefore an enlargement of the stop faces so as to maximise the strength of the system.

According to another arrangement, a method of limiting a maximum dose that may be set in a drug delivery device is provided. The method includes providing a cartridge of medication in said drug delivery device, providing a rotatable shaft, and providing a helical groove along a surface of the rotatable shaft. The helical groove has a first pitch along a first portion of the rotatable shaft and a second pitch along a second portion, and the first pitch is different from the second pitch. The method further includes disposing a non-rotating member on the helical groove of the shaft, and rotating the shaft during dose setting of said drug delivery device. During the rotation, the shaft is rotated relative to said non-rotating member while said non-rotating member traverses along said groove from a proximal end of said shaft towards a distal end of said shaft. The method further includes selecting a dose greater than the medication remaining in the cartridge and utilizing the non-rotating member to prevent a user from further rotating the shaft and increasing the dose.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 illustrates an arrangement of the drug delivery device with a dose setting mechanism in accordance with the one aspect of the present invention;

FIG. 2 illustrates the drug delivery device of FIG. 1 with a cap removed and showing a cartridge holder;

DETAILED DESCRIPTION

Figure 3:
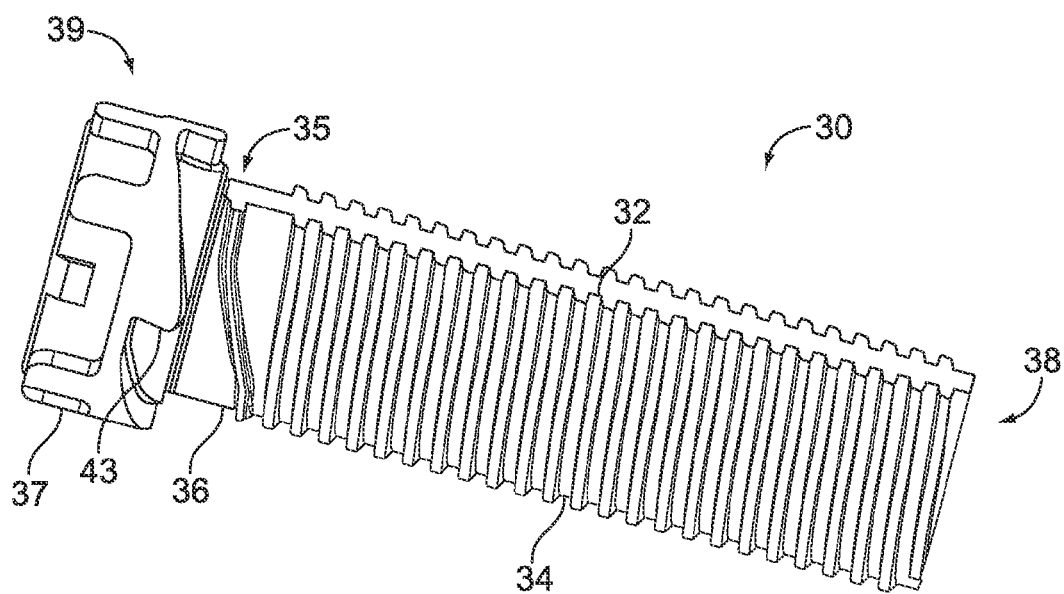
FIG. 3 illustrates a perspective view of a shaft of a dose setting mechanism, such as the dose setting mechanism illustrated in FIG. 1 or 2.

The terms "drug" or "medicinal product" or "medicament", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Referring to FIG. 1, there is shown a drug delivery device 1 in accordance with an exemplary arrangement. The drug delivery device 1 comprises a housing having a first cartridge retaining part 2, and a dose setting mechanism 4. The drug delivery device may be a resettable drug delivery device (i.e., a reusable device) or alternatively a non-resettable drug delivery device (i.e., a non-reusable device). A first end of the cartridge retaining part 2 and a second end of the dose setting mechanism 4 are secured together by connecting features. For non-resettable devices, these connecting features would be permanent and non-reversible. For resettable devices, these connecting features would be releasable.

In this illustrated arrangement, the cartridge housing 2 is secured within the second end of the dose setting mechanism 4. A removable cap 3 is releasably retained over a second end or distal end of a cartridge retaining part or cartridge housing. The dose setting mechanism 4 comprises a dose dial grip 12 and a window or lens 14. A dose scale arrangement 16 is viewable through the window or lens 14. To set a dose of medication contained within the drug delivery device 1, a user rotates the dose dial grip 12 such that a dialled dose will become viewable in the window or lens 14 by way of the dose scale arrangement 16.

FIG. 2 illustrates the medical delivery device 1 of FIG. 1 with the cover 3 removed from a distal end 19 of the medical delivery device 1. This removal exposes the cartridge housing 6. As illustrated, a cartridge 25 from which a number of doses of a medicinal product may be dispensed, is provided in the cartridge housing 6. Preferably, the cartridge 25 contains a type of medicament that can be administered relatively often, such as once or more times a day. One such medicament is either long acting or short acting insulin or an insulin analog. The cartridge 25 comprises a bung or stopper (not illustrated in FIG. 2) that is retained near a second end or a proximal end 27 of the cartridge 25. The medical delivery device, in particular the dose setting mechanism 4, also comprises a driver having a spindle (not illustrated in FIG. 2).

The cartridge housing 6 has a distal end 23 and a proximal end 27. Preferably, the cartridge distal end 23 of the cartridge housing 6 comprises a groove 8 for attaching a removable needle assembly (not illustrated in FIG. 2). However, other needle assembly connection mechanisms could also be used. If the drug delivery device 1 comprises a resettable device, the cartridge proximal end 27 is removably connected to the dose setting mechanism 4. In one preferred embodiment, cartridge housing proximal end 27 is removably connected to the dose setting mechanism 4 via a bayonet connection. However, as those of ordinary skill in the art will recognize, other types of removable connection methods such as threads, partial threads, ramps and detents, snap locks, snap fits, and luer locks may also be used.

As previously mentioned, the dose setting mechanism 4 of the drug delivery device illustrated in FIG. 1 or 2 may be utilized as a reusable drug delivery device (i.e., a drug delivery device that can be reset). Where the drug delivery device 1 comprises a reusable drug delivery device, the cartridge 25 is removable from the cartridge housing 6. The cartridge 25 may be removed from the device 1 without destroying the device 1 by merely having the user disconnect the dose setting mechanism 4 from the cartridge housing 6.

In use, once the cap 3 is removed, a user can attach a suitable needle assembly to the groove 8 provided at the distal end 23 of the cartridge housing 6. Such needle assembly may be, for example, screwed onto a distal end 23 of the housing 6 or alternatively may be snapped onto this distal end 23.

After use, the replaceable cap 3 may be used to re-cover the cartridge housing 6. Preferably, the outer dimensions of the replaceable cap 3 are similar or identical to the outer dimensions of the dose setting mechanism 4 so as to provide an impression of a unitary whole when the replaceable cap 3 is in position covering the cartridge housing 6 when the device is not in use.

In accordance with an exemplary arrangement, it may be beneficial to limit a maximum dose that may be set in the drug delivery device of FIGS. 1 and 2 when a user attempts to set a dose that is greater than the amount of medication remaining in the cartridge. In order to achieve limiting a maximum dose, the dose setting mechanism 4 of drug delivery device 1 preferably includes a last dose lock-out mechanism. The last dose lock-out mechanism preferably includes a rotatable shaft 30 having a helical groove 32 comprising at least a first and second pitch.

Figure 4:
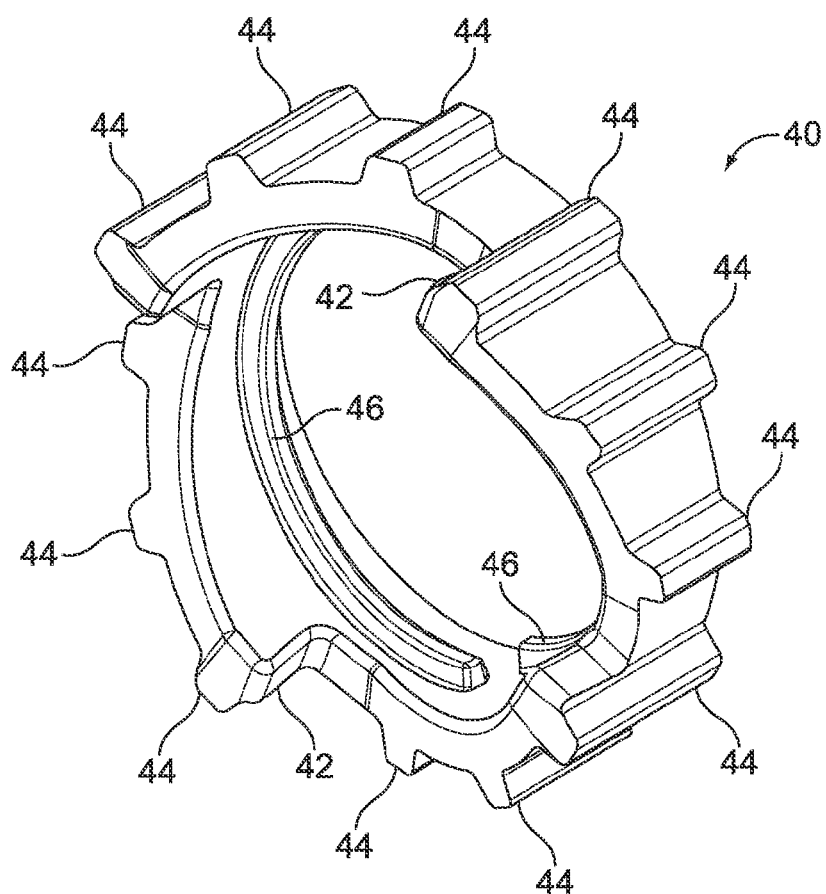
FIG. 4 illustrates a perspective view of a nut member of a dose setting mechanism, such as the dose setting mechanism illustrated in FIG. 1 or 2.

FIGS. 3 and 4 illustrate components of a dose setting mechanism of a drug delivery device, such as the dose setting mechanism 4 of the drug delivery device 1. The dose setting mechanism comprises a last dose lock-out mechanism that prevents a user of the drug delivery device 1 from setting a dose of medication that is greater than the medication remaining in the cartridge of medication. Specifically, FIG. 3 illustrates a rotatable shaft 30 of the last dose lock-out mechanism and FIG. 4 illustrates a non-rotating nut member 40 of the last dose lock-out mechanism. These two components may be coupled together in the dose setting mechanism, as shown in FIGS. 5-11. In an alternative embodiment the nut member may be rotatable and the shaft may be non-rotating. It is important that the nut member 40 and the shaft 30 rotate relative to each other when the user sets a dose.

Referring to FIG. 3, the rotatable shaft 30 comprises a helical groove 32 provided along the rotatable shaft 30. The helical groove has a first pitch provided along a first portion 34 of the rotatable shaft 30 and a second pitch provided along a second portion 36 of the rotatable shaft. The first portion is located near a distal end 38 of the rotatable shaft and the second portion is located near a proximal end 39 of the rotatable shaft. Further, the first pitch is different from the second pitch. In an exemplary embodiment, the second pitch is greater than the first pitch, as depicted in FIG. 3. As just one example, the second pitch may be about 2 to about 10 times the width of the first pitch.

In an exemplary embodiment, a third pitch is provided on a third portion 35 of the rotatable shaft. The third pitch is preferably provided at the end of the second pitch and is preferably different from the second pitch. In an exemplary embodiment, the third pitch is less than the second pitch. The third pitch provided along the third portion 35 may be the same or similar to the first pitch provided along the first portion 34 of the rotatable shaft 30. Alternatively, the third pitch provided along the third portion 35 may be different from the first pitch provided along the first portion 34 of the rotatable shaft 30. The third pitch is preferably the same or very similar in width to the first pitch or alternatively the pitch on the non-rotating member (40).

The rotatable shaft 30 also includes a proximal stop mechanism 37 located at the proximal end 39 of the rotatable shaft 30. Preferably, the shape of the proximal stop mechanism 37 is complementary to the one of the non-rotating member 40, which is illustrated in FIG. 4. In a preferred embodiment the shaft 30 is part of a drive sleeve of the dose setting mechanism 4, preferably accommodated at the distal end of the drive sleeve.

The non-rotating member 40 may comprise a nut. For instance, the non-rotating member may be a complete circular nut, as depicted in FIG. 4. However, the non-rotating member could alternatively be a partial nut.

The non-rotating member 40 includes at least one substantially radial stop face 42. The at least one substantially radial stop face 42 is preferably complementary to at least one stop face 43 on the proximal stop mechanism 37. In an exemplary embodiment, the non-rotating member 40 comprises a plurality of radial stop faces 42. In embodiments of the dose setting mechanism, the length a of the stop face (depicted in FIG. 11) is preferably within a range of about from 0.5 to about 2 mm. However, there is no limit to the length of such stop face as it will generally depend on the design of the device. As such, it may be determined, in part, by certain engineering or design requirements such as an adequate strength for the size of the features based on certain testing parameters, such as Finite Elemental Analysis (FEA).

Further, the non-rotating member 40 comprises a thread form 46 on its interior. Thread form 46 could be a partial thread. In an exemplary embodiment, the thread form 46 comprises two half turns of a two start thread. Other types of thread forms are possible as well. The non-rotating member 40 is capable of being disposed on the helical groove of the rotatable shaft 40, as shown in FIGS. 5-11. The thread form 46 allows the non-rotating member to traverse the helical groove 32 when the rotatable shaft 30 is rotated during dose setting.

The non-rotating member 40 also includes at least one spline feature 44. The spline features 44 may be protrusions from the non-rotating member 40 that may interact with a housing of the drug delivery device 1 that houses the dose setting mechanism 4. The spline feature 44 operates to prevent relative rotation between the non-rotating member 40 and a housing of the drug delivery device that houses the dose setting mechanism 4. In an exemplary embodiment, the non-rotating member comprises a plurality of spline features 44.

During dose setting of a drug delivery device having a dose setting mechanism with the components illustrated in FIGS. 3 and 4, the shaft 30 is rotated relative to the non-rotating member 40. During rotation, the non-rotating member 40 traverses along the helical groove 32 from the distal end 38 toward the proximal end 39 of the shaft 30. The non-rotating member 40 traverses along the helical groove 32 until a dose greater than the medication remaining in the cartridge is selected. When a dose greater than the medication remaining in the cartridge is selected, the non-rotating member 40 prevents the shaft from rotating and increasing the dose dialled. Specifically, the stop faces 42 and 43 prevent the shaft from rotating and increasing the dose dialled.

Figure 5:
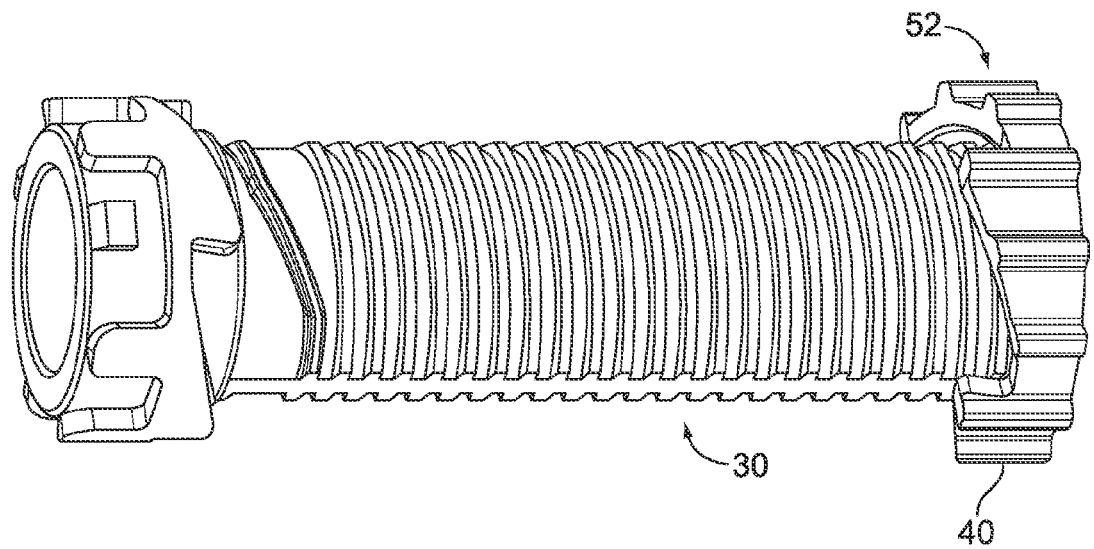
FIG. 5 illustrates a perspective view of the shaft of a dose setting mechanism coupled to a nut member of a dose setting mechanism, such as the dose setting mechanism illustrated in FIG. 1 or 2.
Figure 6:
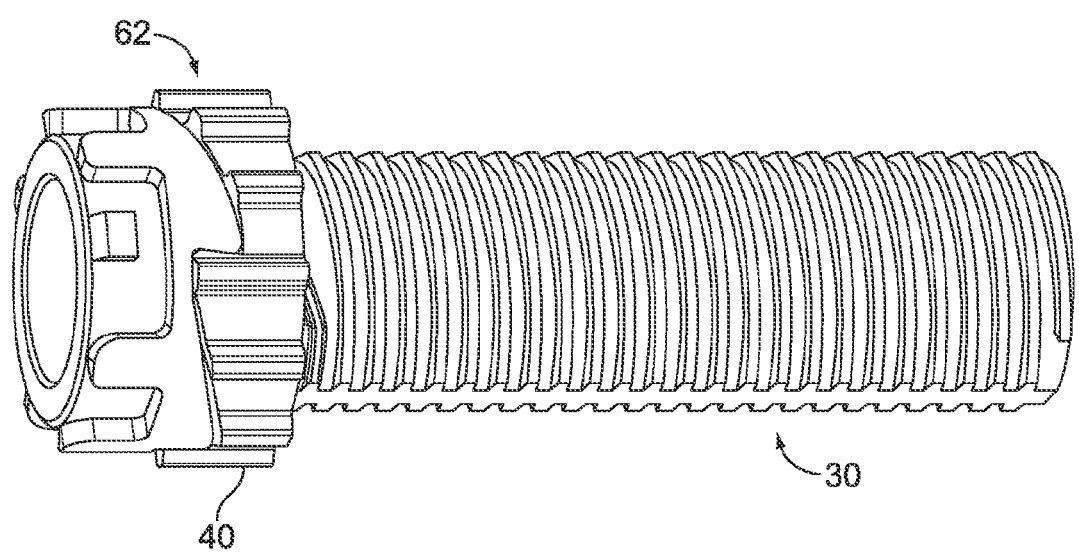
FIG. 6 illustrates a perspective view of the shaft of a dose setting mechanism coupled to a nut member of a dose setting mechanism, such as the dose setting mechanism illustrated in FIG. 1 or 2.

As depicted in FIG. 5, the rotatable shaft 30 comprises a distal start position 52. The non-rotating member 40 is located at the distal start position 52 when the drug delivery device cartridge is substantially filled with medication. Further, as depicted in FIG. 6, the rotatable shaft also comprises a proximal stop position 62. The proximal stop position 62 is located at the point the non-rotating member 40 encounters the proximal stop mechanism 37. The non-rotating member 40 is located at the proximal stop position when the dose dialled equals the amount of medication remaining in the cartridge. A distance between the distal start position 52 and proximal stop position 62 corresponds to an amount of medication contained in the medication cartridge of the drug delivery device. For instance, in the case of a cartridge housing 300 International Units ("units") of medication, there are approximately 300 units of medication when the non-rotating member is located at the distal start position 52. Further, the non-rotating member is located at the proximal stop position 62 when there are no additional units of medication available.

Still further, the non-rotating member is located approximately half-way between (not depicted) the distal start position 52 and proximal stop position 62 when there are approximately 150 units of medication available for dosing.

Alternatively, the non-rotating member 40 during dose dialling may traverse along the helical groove 32 from the proximal end, i.e. a proximal start position, toward the distal end of the shaft 30, i.e. a distal stop position. When a dose greater than the medication remaining in the cartridge is selected, the non-rotating member 40 prevents the shaft 30 from rotating and increasing the dose dialled encountering a distal stop mechanism after reaching the distal stop position.

When the set dose is dispensed from the cartridge, the non-rotating member 40 does not rotate relative to the rotatable shaft 30. Rather, both the non-rotating member 40 and the shaft 30 move in an axial direction.

The operation of the dose setting mechanism will be further described with reference to FIGS. 7-11. For the majority of dose setting, the non-rotating member traverses along the first pitch while traversing along the helical groove 32. However, when the user is setting a dose that is near the limit of the medication remaining in the cartridge 25, the non-rotating member 40 traverses along the helical groove 32 having a second pitch, which is greater than the first pitch. FIGS. 7-11 illustrate the interaction between rotatable shaft 30 and the non-rotating member 40 during dose setting of the last dose. Specifically, these Figures illustrate the last approximately 90 degrees of rotation of the rotatable shaft 30. In such an arrangement, the last approximately 90 degrees of rotation may be generally equivalent to about 4 to about 7 units of medication contained in the cartridge 25 of the injection device. For purposes of clarity, the spline features 44 of the non-rotating member 40 have been omitted. The FIGS. 7-11 depict the relative rotation between the non-rotating member 40 and the rotatable shaft 30.

Figure 7:
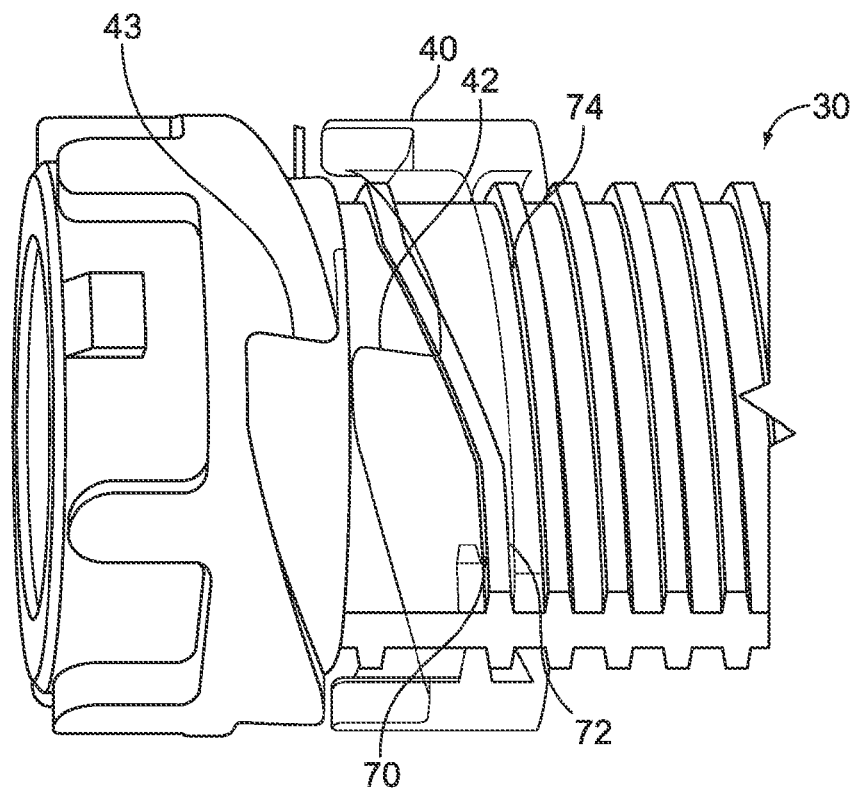
FIG. 7 illustrates a partial perspective view of the shaft of a dose setting mechanism coupled to a nut member of a dose setting mechanism during dose setting, such as the dose setting mechanism illustrated in FIG. 1 or 2.

FIG. 7 depicts the beginning of the last 90 degrees of rotation, where, in this example, the stop feature 42 of the non-rotating member and stop feature 43 of the rotatable shaft 30 just pass each other. At this point, the non-rotating member 40 is traversing along the first pitch and is just about to begin traversing along the second pitch. The threads of the non-rotating member 40 contact the threads of the rotatable shaft 30 in, for example, areas 70, 72, and 74.

Figure 8:
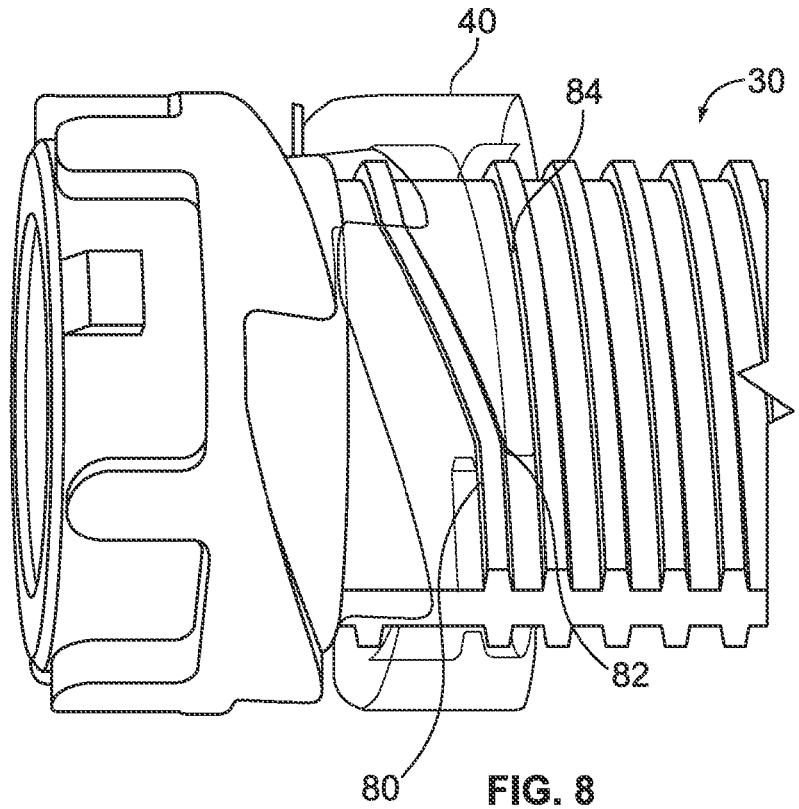
FIG. 8 illustrates a partial perspective view of the shaft of a dose setting mechanism coupled to a nut member of a dose setting mechanism during dose setting, such as the dose setting mechanism illustrated in FIG. 1 or 2.

FIG. 8 depicts when the non-rotating member 40 begins traversing along the second pitch. The threads of the non-rotating member 40 contact the threads of the rotatable shaft 30 at, for example, point 82 and areas 80 and 84. In this example, the second pitch begins at a location corresponding to approximately the last 80 degrees of rotation. However, it should be understood that the second pitch could begin at a different location. For example, the second pitch could begin at a location corresponding to approximately the last 45-360 degrees of rotation. Other locations are possible as well.

Figure 9:
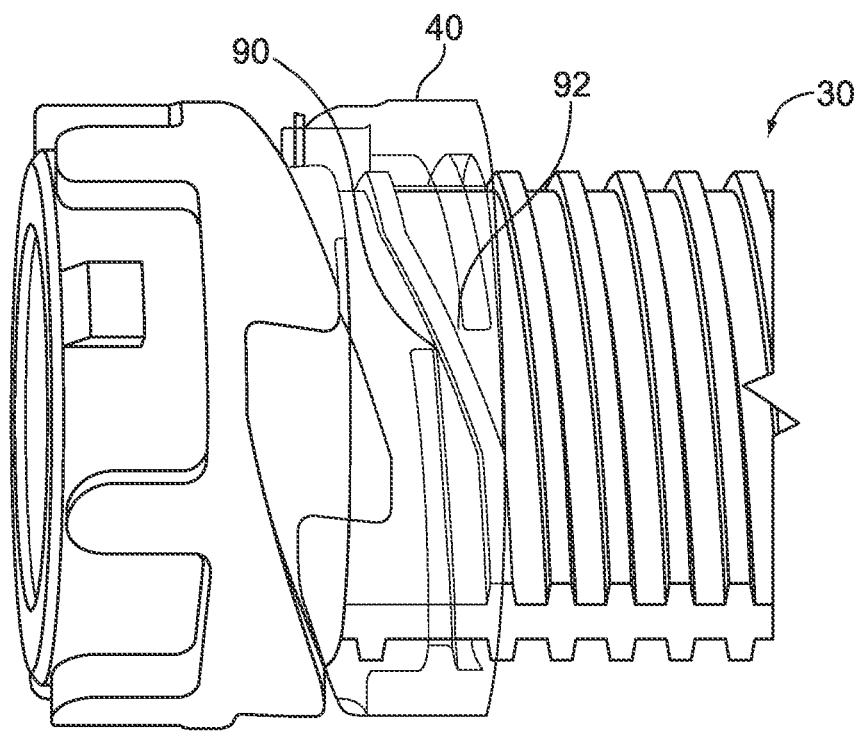
FIG. 9 illustrates a partial perspective view of the shaft of a dose setting mechanism coupled to a nut member of a dose setting mechanism during dose setting, such as the dose setting mechanism illustrated in FIG. 1 or 2.

FIG. 9 depicts when the non-rotating member 40 is approximately midway through traversing along the second pitch where it travels fast compared to the travelling along the first pitch. This means that the axial displacement of the non-rotating member 40 relative to the shaft 30 over a certain angle of rotation along the second pitch is greater than the axial displacement of non-rotating member 40 relative to shaft 30 over the same angle of rotation along the first pitch. The fast rotation along the second pitch may be sensed by the user indicating that the end of the dose settable amount is reached. At the position illustrated in FIG. 9 the threads of the non-rotating member 40 contact the threads of the rotatable shaft 30 only at points 90 and 92. As FIG. 9 depicts, the nut 40 is adequately guided on both sides due to the twin start threads 46 when it is engaged with the second pitch section. However, the contact area between the threads is minimal. As shown, the twin start threads contact the second pitch area at points 90 and 92. These contact points prevent the non-rotating member 40 from twisting off axis during this increased pitch segment.

Figure 10:
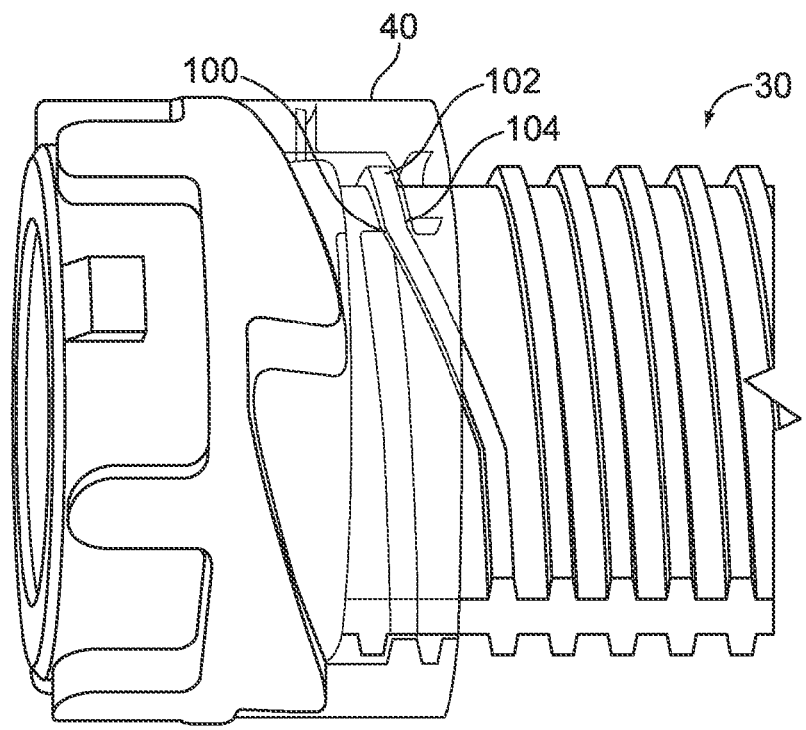
FIG. 10 illustrates a partial perspective view of the shaft of a dose setting mechanism coupled to a nut member of a dose setting mechanism during dose setting, such as the dose setting mechanism illustrated in FIG. 1 or 2.

FIG. 10 depicts when the non-rotating member 40 begins traversing along the third pitch, and also just before the stop feature 42 and stop feature 43 engage. The threads of the non-rotating member 40 contact the threads of the rotatable shaft 30 at, for example, points 100 and 104 and in area 102.

Figure 11:
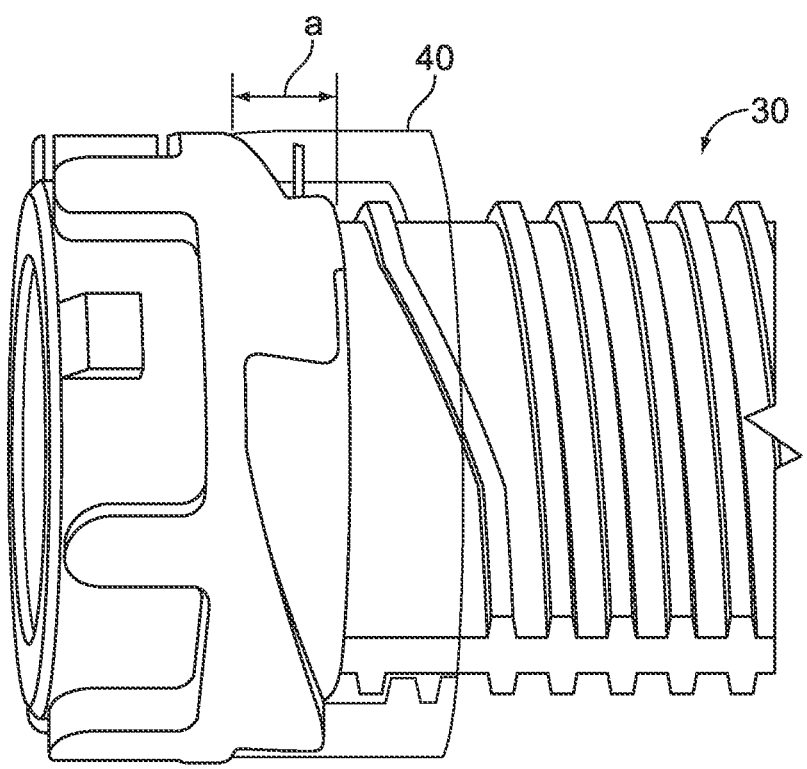
FIG. 11 illustrates a partial perspective view of the shaft of a dose setting mechanism coupled to a nut member of a dose setting mechanism during dose setting, such as the dose setting mechanism illustrated in FIG. 1 or 2.

FIG. 11 depicts when the non-rotating member 40 is finished traversing along the third pitch and when the stop feature 42 and stop feature 43 engage. As FIG. 11 depicts, the stop face 42 of the non-rotating member abuts a complementary stop face 43 of the distal stop mechanism 37 of the rotatable shaft 30. The effective length of the stop faces is shown as the length a. Beneficially, the greater the effective length, the greater the stop force of the last dose lock-out mechanism.

By providing the second pitch rather than just a constant pitch on the rotatable shaft, the effective length a of the stop faces in axial direction can be increased. The change of pitch on the rotatable shaft 30 from a first pitch to the increased second pitch allows for an increase in the effective length a of the stop faces 42, 43 and therefore creates an increased stop face contact area. The increased stop face contact area increases the stop force when a user attempts to dial a dose greater than the amount of medication remaining in the cartridge.

In addition, the reduced pitch section (i.e., the third pitch on third portion 35) is preferably similar to or identical to the pitch on the nut 40. Therefore, the surface engagement between the threads 46 of the non-rotating member 40 and the threads of the rotatable shaft 30 is increased, thus enabling a higher axial load to be restrained. Because a higher axial load can be restrained due to the increased surface engagement, there is a reduced risk of damage to the threads on these two parts when a high stop torque load is applied by a user. The longer the reduced pitch on third portion 35, the larger the contact surface between the thread forms and therefore the higher the axial load that these thread forms can restrain.

It should be understood that the example depicting the last 90 degrees of rotation in FIGS. 7-11 is for illustrative purposes and is not meant to be limiting. For example, the second pitch could occur at or near the last 180 degrees of rotation (i.e., the final one-half turn of the rotatable shaft relative to the non-rotating member.). Still further, the second pitch could occur at or near the last 360 degrees of rotation (i.e., the final complete turn of the rotatable shaft relative to the non-rotating member.). Still further, the second pitch could occur at or near the last 540 degrees of rotation (i.e., the final one and a half turns of the rotatable shaft relative to the non-rotating member). As one of ordinary skill in the art will recognize, other examples are possible as well.

A dose setting mechanism in accordance with an exemplary embodiment increases the stop face area without having a detrimental effect on the stop strength. Accordingly, a dose setting mechanism in accordance with an exemplary embodiment offers an improved last dose lock-out mechanism with an increased stop force. The increased stop force is useful for preventing a user from dialling a dose greater than the remaining medication. As discussed above, the dose setting mechanism described above may be utilized in drug delivery devices that are reusable or in drug delivery devices that are non-reusable.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A dose setting mechanism for a drug delivery device, with a cartridge of medication, wherein the dose setting mechanism is operable to select a dose of medication which shall be administered out of said cartridge, the dose setting mechanism comprising:
   a shaft comprising a helical thread having three separate portions, a first portion having a first pitch followed by a second portion having a second pitch that is larger than the first pitch and a third portion following the second portion having a third pitch that is less than the second pitch;
   a nut member disposed on said helical thread of said shaft, wherein during dose setting of said drug delivery device, said shaft is rotated relative to said nut member while said nut member traverses in longitudinal direction along said helical thread from a first end of said shaft towards a second end of said shaft;
   where the nut member and shaft are configured to engage each other to form a stop mechanism to prevent a user of said dose setting mechanism from setting a dose of said medication that is greater than said remaining medication in said cartridge, the stop mechanism further comprising a radial stop face on the nut member, and a counter radial stop face on the shaft configured to engage the radial stop face on the nut member to prevent the shaft from rotating relative to the nut member.

2. The mechanism of claim 1 wherein the relative movement of shaft and nut member comprises a start position and a stop position of shaft and nut member relative to each other, wherein the displacement distance of the nut member between said start position and said stop position along the shaft corresponds to the amount of medication contained in said cartridge.

3. The mechanism of claim 1 wherein when said dose is dispensed from said cartridge, said nut member does not rotate relative to said shaft but rather both said nut member and said shaft move in a substantially axial direction, wherein said nut member comprises at least one spline feature, said at least one spline feature preventing relative rotation between said nut member and a housing of said drug delivery device.

4. The mechanism of claim 1 wherein said nut member comprises a partial thread, two half turns of a two start thread.

5. The mechanism of claim 1 wherein said first portion is located near a proximal end of said shaft and said second portion is located near a distal end of said shaft.

6. The mechanism of claim 1 wherein said nut member comprises a plurality of substantially radial stop faces, said plurality of radial stop faces engaging a plurality of substantially radial stop faces on said shaft.

7. The mechanism of claim 1 wherein said drug delivery device comprises a non-reusable pen type drug delivery device.

8. The mechanism of claim 1 wherein said nut member is a complete circular nut.

9. The mechanism of claim 1, wherein the second portion begins at a location corresponding to the last 45 to 360 degrees of rotation when the shaft is rotated relative to said nut member prior the nut member reaches the stop position.

10. The mechanism of claim 1 wherein said first end of said shaft comprises a distal end and said second end of said shaft comprises a proximal end.

11. The mechanism of claim 1 wherein the shaft is rotatable and the nut member is non-rotating.

12. A drug delivery device comprising a dose setting mechanism according to claim 1 and a cartridge of medication.

* * * * *